United States Patent [19]

Born et al.

[11] Patent Number: 5,399,338
[45] Date of Patent: Mar. 21, 1995

[54] ENHANCEMENT OF ABNORMAL TISSUE UPTAKE OF ANTIBODIES, TUMOR-SPECIFIC AGENTS OR CONJUGATES THEREOF FOR DIAGNOSTIC IMAGING OR THERAPY

[75] Inventors: Jerry L. Born; Dennis Eshima; Paul L. Mann; Nicholas A. Matwiyoff; Buck A. Rhodes, all of Albuquerque, N. Mex.

[73] Assignee: University of New Mexico, Albuquerque, N. Mex.

[21] Appl. No.: 694,151

[22] Filed: May 1, 1991

[51] Int. Cl.$^6$ .................. A61K 49/02; A61K 49/00; A61K 39/395
[52] U.S. Cl. ...................... 424/1.49; 424/9; 424/4; 424/182.1
[58] Field of Search ............ 424/1.1, 9, 85.91, 4, 424/7.1, 1.69, 1.65, 1.45, 1.49, 1.53; 530/396

[56] References Cited

U.S. PATENT DOCUMENTS

| | | | |
|---|---|---|---|
| 4,816,462 | 3/1989 | Nowicky | 514/279 |
| 4,970,212 | 11/1990 | Nowicky | 514/279 |
| 5,021,427 | 6/1991 | Elbein et al. | 548/452 X |
| 5,053,386 | 10/1991 | Tung | 514/2 |
| 5,240,693 | 8/1993 | Born et al. | 424/4 |

OTHER PUBLICATIONS

Thakur et al., "Evaluation of Biological Response Modifiers in the Enhancement of Tumor Uptake of Technetium-99m Labeled Macromolecules," *J. of Immunol. Meth.*, vol. 152, pp. 209–216 (1992).

Nowicky et al., "Macroscopic UV-Marking through Affinity," Journal of Tumor Oncology, vol. 3, No. 4, 1988, 3 pages.

Sabbour et al. (ed.), "V Mediterranean Congress of Chemotherapy", 26/10–Jan. 11, 1986, Cairo, Egypt, Proceedings, Chemioterapia, Supplement to No. 2, vol. 6, Jun. 1987.

Mann et al., "Cell Surface Oligosaccharide Modulation during Differentiation: IV. Normal and Transformed Cell Growth Control," *Mechanisms of Ageing and Development*, 44 (1988), pp. 17–33.

*Primary Examiner*—Robert L. Stoll
*Assistant Examiner*—John M. Covert
*Attorney, Agent, or Firm*—Mille, White, Zelano, & Branigan

[57] ABSTRACT

Biomodulators, in conjunction with antibodies, tumor-specific agents or conjugates thereof, optionally linked to imaging-active moieties, can be administered to a host to enhance images thereof, e.g., NMR-, X-ray- or radioimages, preferably by increasing aberrant tissue signal intensity.

15 Claims, 6 Drawing Sheets

ENHANCEMENT OF ABNORMAL TISSUE UPTAKE OF ANTIBODIES, TUMOR-SPECIFIC AGENTS OR CONJUGATES THEREOF FOR DIAGNOSTIC IMAGING OR THERAPY

This application is related to Ser. No. 07/694,321, now abandoned; Ser. No. 07/694,325, pending; Ser. No. 07/694,157, now U.S. Pat. No. 5,240,693; all entirely incorporated by reference herein.

BACKGROUND OF THE INVENTION

One of the most difficult problems in in vivo imaging of living organisms is how to distinguish between normal and aberrant tissue. Many approaches to this problem have been developed, including inter alia, X-ray imaging (including CAT-scanning), radionuclide imaging, fluoroscopy, ultrasonic imaging and nuclear magnetic resonance (NMR) imaging (MRI), with and without the administration of imaging agents, e.g., contrast media. The imaging agent may comprise materials which are themselves opaque to the detection signal and simply increase the contrast between organs or tissues containing it and organs or tissues which do not, e.g., as with X-ray agents. Alternatively, the agent can be one which has a local effect on the endogenous moiety active to the modality, as in the effect of NMR contrast agents on protons in vivo. For example, such agents may comprise materials which are selectively biodistributed due to pharmacokinetics or affinity for a certain compound, cell type, tissue, organ etc. In the latter case, the agent will highlight those areas containing the matter for which the agent, e.g., based on an antibody e.g., a monoclonal antibody, has affinity, e.g., a cell-surface antigen. In the former, it will highlight the areas where it is selectively transported. Many such imaging agents are well known in the relevant arts, as are methods of use thereof.

A number of methods have been explored for enhancing tumor uptake of monoclonal antibodies.

One approach is the use of interferons to augment tumor antigen expression. J. W. Greiner et al., "Augmentation of Tumor Antigen Expression by Recombinant Human Interferons: Enhance Targeting of Monoclonal Antibodies to Carcinomas," Cancer Imaging with Radiolabeled Antibodies, D. M. Goldenberg ed., Kluwer Academic Publishers, Boston, pp. 413–432 (1990). One problem with this approach is that the effect is limited to certain antigens and thus cannot be applied to a broad spectrum of tumors and antibodies. This method does not increase the accessibility of the antibody to the tumor, but by increasing available binding sites may increase the target-to-non-target ratio.

Anti-antibodies have been used to clear out circulating radiolabeled antibody and hence improve the target-to-non-target ratios of radioisotope in the tumor compared to the surrounding normal tissue. R. M. Sharkey et al., "Anti-Antibody Enhancement of Tumor Imaging," Cancer Imaging with Radiolabeled Antibodies, D. M. Goldenberg ed., Kluwer Academic Publishers, Boston, pp. 433–455 (1990). An alternative to this approach is the use of exchange diffusion to remove unbound radiolabeled antibody from the circulation. C. Henry et al., "Improved Monoclonal Antibody Tumor/Background Ratios with Exchange Transfusions," Antibody Immunoconjugates Radiopharm. 4, 22 (1991). Both methods function by decreasing the background, and hence do not enhance uptake of the radiolabeled antibody in the tumors.

Vasodilators have been conjugated to antibodies to enhance their uptake. B. LeBerthon et al, "The Development of a Novel Vasoactive Immunoconjugate to Enhance the Uptake of Monoclonal Antibodies in Tumors," Antibody Immunoconjugates Radiopharm. 4, 42 (1991). These investigators coupled human IL-2 to antibodies and demonstrated a 3-fold increase in tumor uptake. The problem with this method is that it requires the production of a complex molecule. External beam radiation focused on tumors has been used by S. E. Order et al. to enhance tumor uptake or radiolabeled antibodies administered for radiotherapy of tumors. J. S. Msirikale et al., "Radiation Enhancement of Radiolabeled Antibody Depositions in Tumors," Int. J. Radiat. Oncol. Biol. Phys. 13(12), 1839–44 (1987). The external beam radiation presumably causes increased vascular permeability in the tumor thereby enhancing uptake of the radiolabeled antibody. This study used 131-I labeled anti-ferritin for targeting hepatoma, preceded by external radiation.

Tumor necrosis factor TNF-α has been used in conjunction with a monoclonal antibody immunoconjugate and shown to enhance tumor uptake, while IL-1 and IL-2 used in conjunction with a monoclonal antibody immunoconjugate does not enhance antibody targeting. G. A. Pietersz et al., "The Use of Immunoconjugates in Conjunction with Biological Response Modifiers," Antibody Immunoconjugates Radiopharm. 4, 205 (1991).

One major difference between the use of biological response modifiers to enhance antibody targeting to tumors and biomodulators is that biological response modifiers produce a more generalized or non-specific effect, while the biomodulators preferentially effect change in aberrant or abnormal tissue. The biomodulators may induce the secretion of biological response modifiers in situ so that the effect is more localized than that obtained by systemic administration of a biological response modifier. Thus, one hypothesis is that biomodulators induce biologic response modifiers within tumors causing a localized reaction which results in enhanced tumor uptake of a radiolabeled antibody in the circulation during the induced response. Because the action is localized, biomodulators are less toxic than biologic response modifiers.

Each of the known agents and methods suffers from a variety of deficiencies related to tolerability of the imaging agent, invasive nature of the active radiation and efficiency and accuracy of the diagnosis enabled by the resulting image. For example, NMR imaging is the most safe in terms of the radiation used. It does not involve ionizing radiation as do X-ray and radiodiagnostics.

Under many circumstances each modality provides very detailed information by imaging of various tissues. However, each suffers from a limitation based upon the lack of distinction between normal and aberrant tissue which has the same signature. Several approaches have been taken toward increasing the specificity of contrast agents (often in combination with targeting agents, e.g., antibodies and small biomolecules), thereby expanding the applicability of a given modality. However, even such improvements are insufficient, e.g., suffering from insufficient tissue specificity (target tissue-to-non-target tissue ratios), insufficient target tissue uptake on an absolute basis, insufficiently rapid pharmacokinetics of tissue uptake, etc.

What is needed is a contrast agent which is of increased specificity for aberrant tissue (e.g., tumors) versus its normal tissue counterpart, and/or of increased and/or more rapid aberrant tissue uptake, etc. Antibody-based drug delivery suffers from analogous defects as described for the imaging area above and analogous improvements are needed.

SUMMARY OF THE INVENTION

Figure 1:
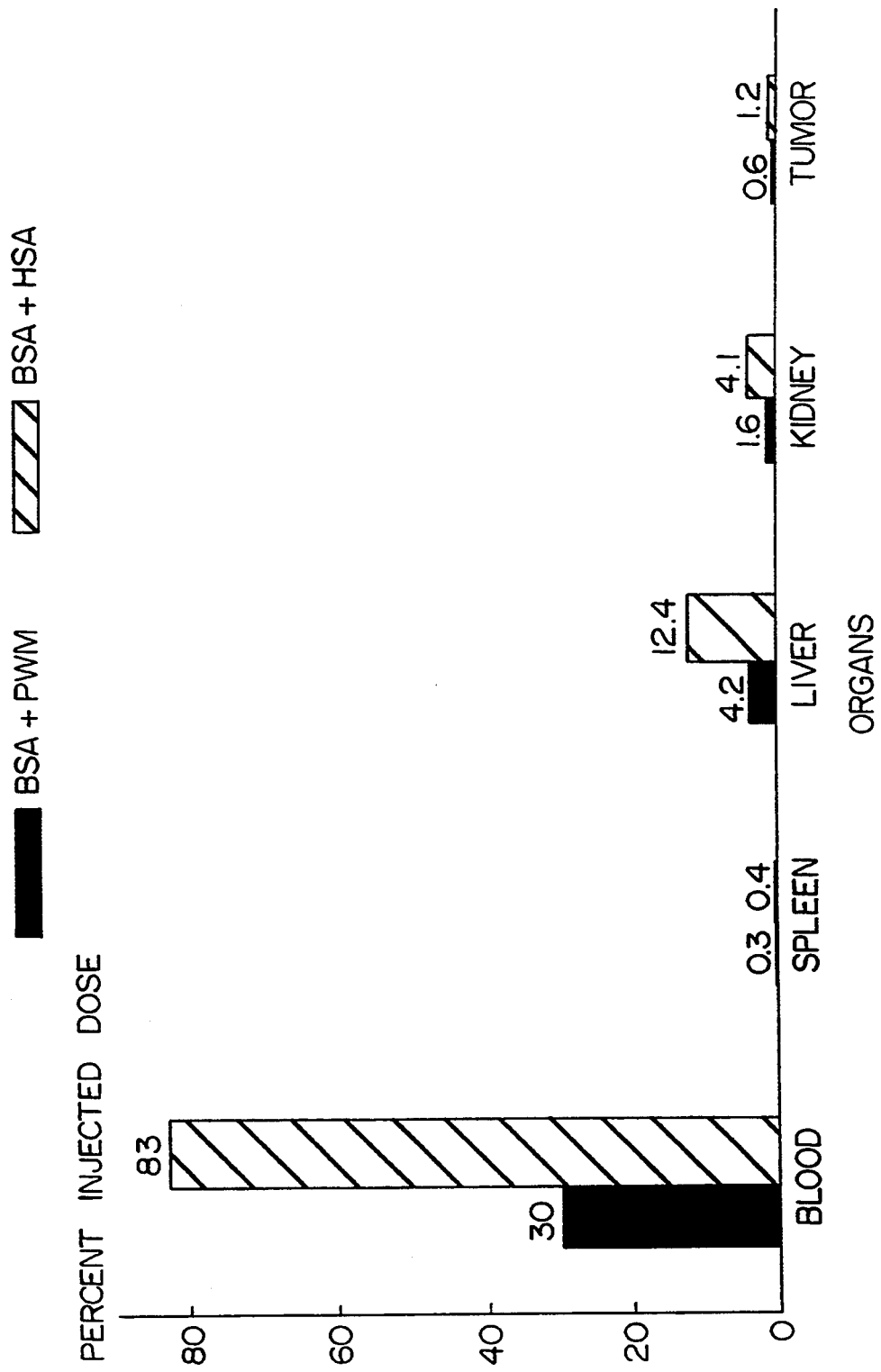
FIG. 1 and FIG. 2 are each plots of $^{125}$I BSA Biodistribution wherein the $^{125}$I BSA is con-injected with either pokeweed mitogen (PWM) or human serum albumin (HSA).

The present invention provides a method of enhancing the delivery to abnormal tissue of an imaging sensitive moiety or therapeutic agent conjugated to an antibody which preferentially interacts with said abnormal tissue in comparison to neighboring normal tissue, comprising administering to a host a biomodulator and said active agent, the relative timing of the administration of each of the biomodulator and the active agent and their amounts being effective to enhance the preferential interaction of said active agent over neighboring normal tissue.

In preferred aspects, inter alia, this invention involves an active agent which is a monoclonal antibody conjugated to an imaging or therapeutic agent; involves an active agent such as the foregoing which is radiolabeled or conjugated to an imaging or therapeutic moiety; involves abnormal tissue which is a tumor; or involves preferred biomodulators such as pokeweed mitogen or Ukrain.

Biomodulators

Biomodulators are natural products or synthetic compounds, e.g., analogs of a natural product which perturb the normal cellular differentiative and proliferative activity of eucaryotic, particularly mammalian, particularly human, cells. This biomodulatory activity is non-cell-lineage specific, affecting differentiation and proliferation in substantially all species and substantially all cell types. The activity of these compounds is considered to be at a primitive level of cellular control, common to all cells, and the compounds are therefore nonspecific in their effect and production by cells. Thus, biomodulators as defined herein are distinct from so-called "biological response modifiers," such as, e.g., interleukins, interferons and other "kines," which have highly specific activities, and which are specific natural products of specific stimuli produced by specific highly specialized cell types. Without wishing to be bound by theory, it is believed that the activity of biomodulators is based upon a generic, cell-surface oligosaccharide dependent model for "primitive" phenotypic expressions of differentiation. This theory is discussed in P. L. Mann, Intl. Rev. Cytol. 12, 67–95 (1988), which is incorporated herein by reference. Preferred "biomodulators" include compounds selected from (a) a compound of formula (I)

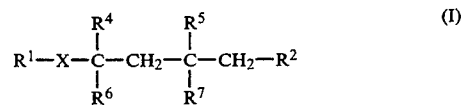

wherein
$R^1$ is an optionally substituted aromatic, cycloaliphatic or heterocyclic ring system,
$R^2$ is —CH$_2$OH, —CHO, —COOR$^3$, —COSR$^3$, —CONR$^{89}$ or the corresponding lactone

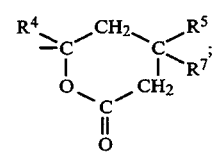

wherein
$R^3$ is H or C$_{1-10}$-alkyl,
$R^4$ and $R^5$ are each independently H or C$_{1-6}$-alkyl,
$R^6$ and $R^7$ are each independently OR, NHR or SR wherein R is H or C$_{1-4}$-alkanoyl,
$R^8$ and $R^9$ are each independently H or C$_{1-10}$-alkyl, and
X is C$_{2-3}$-alkylene, C$_{2-3}$-alkenylene, C$_{2-3}$-alkynylene, a cyclopropylene group, —OCH$_2$— or —SCH$_2$—;

(b) a compound of formula (II) (swainsonine)

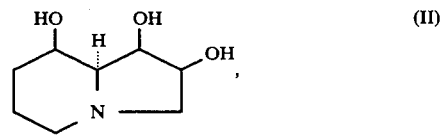

or an indolizidine alkaloid having an electronically similar 1,3-diol structure;

(c) cellular activator and differentiator (CAD);

(d) pokeweed mitogen; and (e) Ukrain, and having the biological activity of a biomodulator as described herein.

A first category of compounds useful in the methods of the present invention comprises compounds of formula (I) as described above. Particularly preferred compounds within the scope of formula (I) are those which have a steric configuration at the 3,5-carbon atoms of the heptanoic or octanoic acid based diol chain which is substantially electronically similar to that of the 3S,5R, 3S,5S or 3R,5R configurations of colletruncoic acid. By "substantially electronically similar" is meant that in the energy minimized form, the interhydroxyl distance between the relevant hydroxyl groups is between 4.2–4.4 Å, preferably about 4.3 Å. The electronic similarity of the compounds can be determined, e.g., by performing routine energy minimization calculations, e.g., utilizing conventional calculations, such as those performed by the Chemdraft Computational Package, program MM-2, (C-Graph Software, Inc., Austin, Tex. 78763). In general, compounds which have a configuration 3R,5S (when X is an alkylene group, i.e., is saturated) or equivalently 3S,5R (when X is an alkenylene or alkynylene group, i.e., is unsaturated) will correspond to this most preferred structure. 3R,5R- and 3S,5S- configurations are also preferred.

The radical $R^1$ has a variable effect. In general, the $R^1$ radical is substantially hydrophobic with well defined pockets of electronegativity, long as it is substantially hydrophobic and preferably electronegative. Suitable $R^1$ ring groups have 1–4 or more fused and/or covalently bonded rings, optionally substituted by substituents which render this portion of the molecule electronegative (e.g., OH, halo, $NO_2$, $NH_2$, COOH, etc.). The compounds of formula I can possess $R^1$ ring groups having a hydrophobicity and/or electronegativity on the order of those of one or more of the following suitable $R^1$ rings, including $C_{6-25}$ mono-, bi-, tri- or polynucleararyl, -aryloxy, -cycloalkyl, -cycloalkenyl, -cycloalkadienyl, etc., as well as heterocyclic rings containing or sharing one or more, e.g., 2 or 3, O, S or N atoms. Where fused systems containing 1–4 or more individual rings are involved, each ring generally contains 4–7 atoms, 1–3, preferably, 1–2, of which are O, N or S atoms, the remainder being C atoms, these generally having 1–4 hetero atoms in total. Thus, heteroaryl and hydroheteroaryl groups are suitable. Examples of suitable $R^1$ groups include benzyl, benzyloxy, phenyl, phenyloxy, naphthyl, naphthyloxy, tetrahydronaphthyl, hexahydronaphthyl, octahydronaphthyl, imidazolyl, pyrimidyl, pyrazolyl, indenyl, quinolinyl, pyrrolyl, indolyl, indolizinyl, etc.

In addition, particularly preferred compounds of formula (I) are those in which n is 1, $R^2$ is $COOR^3$ or the corresponding lactone, $R^4$ and $R^5$ are each H, $R^6$ and $R^7$ are each OH, and X contains a cis or trans double bond.

One subtype of these compounds useful in the methods of the present invention are relatively small (for example, molecular weight less than 1,000 daltons) naturally occurring compounds (in isolated form) having the structure of formula I and the required electronic structure at the 3,5-carbon atoms. For example, the appropriate enantiomer of colletruncoic acid as defined above,

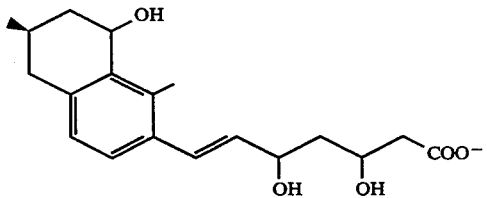

a natural compound isolated from *Colletotrichum truncatum*, has a structure encompassed by the structural formula described above and has been shown to have biomodulator activity. Colletruncoic acid can be isolated according to the method outlined in Stoessl, A., and Stothers, J. B., Z. Naturforsh. 41c, 677–680 (1986), except as modified in that Stoessl et al. described the natural product as being a racemic methylester, which is incorrect; the correct compound is a free acid of one enantiomer with the noted stereochemistry.

Another subtype of these compounds are synthetic compounds of formula I having the required electronic structure at the 3,5-carbon atoms, as described above. All compounds of formula I can be made, in general, from readily available and/or preparable starting materials according to routine chemical syntheses, for example, according to methods outlined in U.S. Pat. Nos. 4,755,606, 4,613,610, 4,255,444, 4,248,889, 4,761,419, 4,751,235, 4,198,425, 4,137,322, 3,983,140, 4,588,715, 4,710,513, 4,739,073, 4,681,893; WO 84/92903; WO 87/02662; WO 88/01997; and WO 86/03488. For joining $R^1—X—C$ (wherein C is the rest of the molecule) when X is $CH_2CH_2$, see Tetrahedron, 42, 4909–4951 (1986). For joining $R^1—X-C$ when X is $—CH{=}CH—$, a selenoxide or sulfoxide coupling and elimination strategy can be employed (see J. Org. Chem., 51, 648–657 (1986)) or, alternatively, Wittig methodology (see J. Org. Chem., 49, 3994–4003 (1984)). When X is $—C{\equiv}C—$, the acetylide $R^1—C{\equiv}C^-$ can be added to an appropriate aldehyde or ketone. When X is $—OCH_2—$ or $—SCH_2—$ then $R^1O^-$ or $R^1S^-$ will be condensed with an appropriate electrophile; see Tetrahedron Lett., 29, 2563–2566 (1988). Similarly, the $R^1$ moieties bearing substituted groups can be synthesized either before or after linkage to the remainder of the molecule.

A second general category of compounds having a related structure and having biomodulator activity is constituted by other small, naturally occurring compounds such as, e.g., swainsonine, 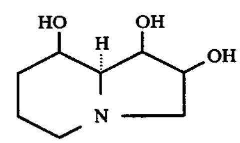 which is a low molecular weight indolizidine alkaloid extracted from Swainsona sp. as well as from a number of other natural sources, and has hydroxy groups on its ring which have an almost identical electronic structure to the hydroxy groups on the heptanoate chain as described above. (Swainsonine is known to have anticancer effects possibly mediated through its inhibition of α-mannosidase II; thus, this effect is not suggestive of its biomodulator role or its range of activities in the other utilities described above. See, e.g., Newton, S. A., et al., J. Natl. Cancer Inst. 81, 1024–1033 (1989); Dennis, J. W., et al., Cancer Res. 50, 1867–1872 (1990).) Swainsonine is commercially available, e.g., from Boerringer-Mannheim, or can be isolated according to the method outlined in Hino, M., et al., J. Antibiotics 38, 926–935 (1985). Other members of this category are, e.g., other indolizidine alkaloid compounds retaining the electronic structure of the important "1,3-diol array" of swainsonine, such as swainsonine substituted in the ortho and meta positions on the 6-membered ring by hydroxy groups (castanospermine) and other natural products having an electronically similar 1,3 diol array. Still other suitable alkaloids are related compounds having two 6-membered rings or two 5-membered rings.

In addition to the known natural low molecular weight compounds swainsonine and colletruncoic acid, a third major type of biomodulator is a new compound provided by the present invention having properties similar to the compounds of Formula I. This compound, cellular activator and differentiator or CAD, is isolated from *Penicillium restrictum*, has a molecular weight of about 500, and is believed, without wishing to be bound by theory, to have a similar structure to colletruncoic acid. It can be isolated according to the method outlined in application Ser. No. 07/694,321.

A fourth category of compounds useful in the methods of the present invention are high molecular weight compounds having biomodulator activity, such as pokeweed mitogen (PWM), which is a well known mixture of five isomitogenic glycopeptides extracted from *Phytolacca americana*, and which is known for its ability to stimulate cellular proliferation. Although its structural relationship to the above described compounds is uncertain, PWM is thought to interact with cells in a similar way and has the same spectrum of effects for the various utilities disclosed herein. Pokeweed mitogen can be isolated according to well-known methods, e.g., according to the method outlined in Riesfeld, R. A., et al., Proc. Natl. Acad. Sci. (U.S.) 58, 2020–2027 (1967). It is noted that the differentiative and proliferative activities of PWM can be separated, i.e., by separating the isotypes, e.g., according to the method of Waxdal, M. J., Biochem. 13, 3671 (1974). The differentiative substance is preferred.

Figure 6:
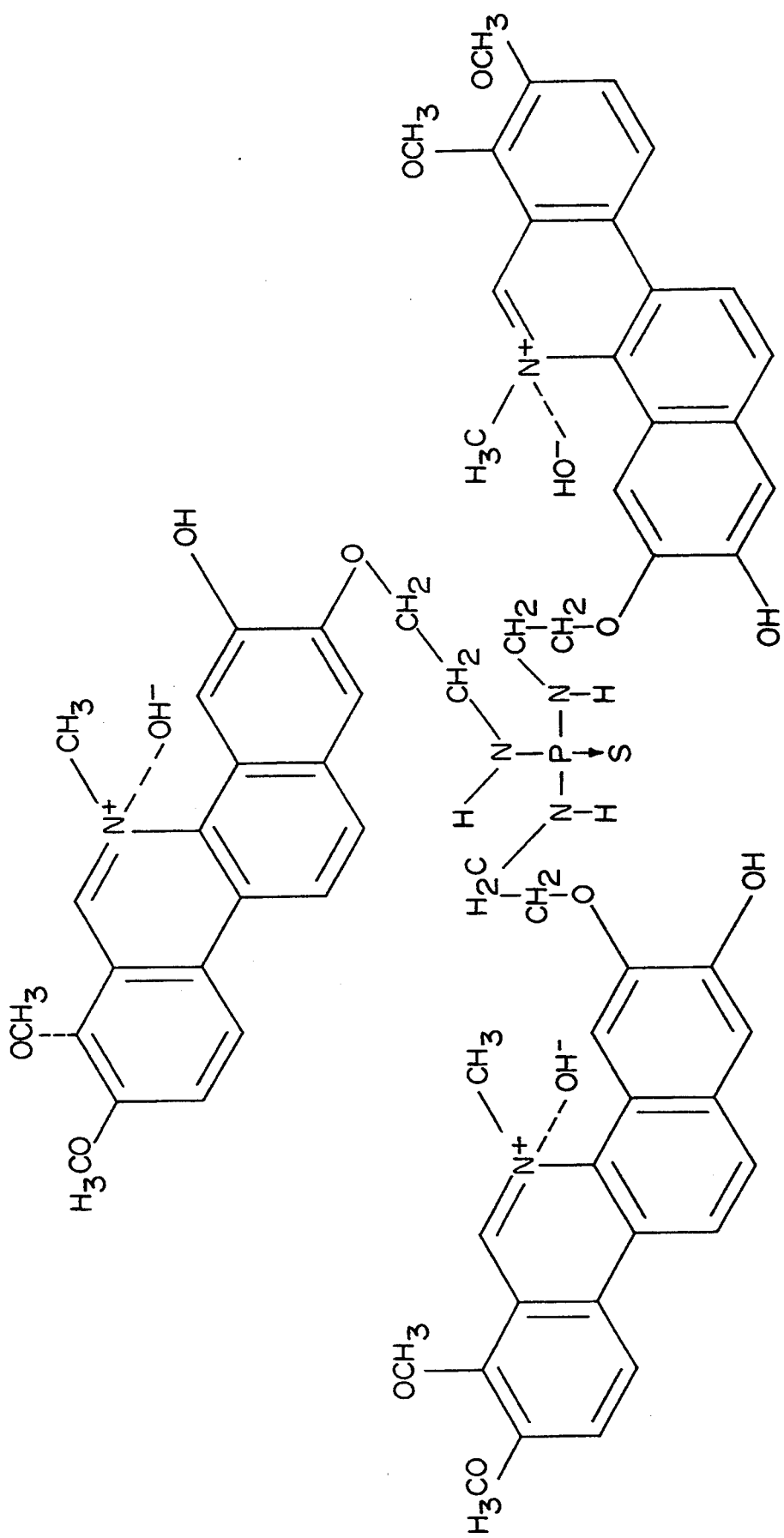
FIG. 6 shows the structure of Ukrain.

A fifth substance can be considered as a biomodulator or equivalent thereto as this term is utilized in this application, i.e., Ukrain. This is a soluble, non-toxic, derivative of an alkaloid found in the sap of greater celandine (*Chelidonium majus L.*). It is marketed in some European countries as an antitumor agent. Its preparation is described in Nowicky, "Cancer treatment using anticancer preparation alkaloid derivative Ukrain," Proceedings of the IV Mediterranean Congress of Chemotherapy, Chemioterapia 4 (Supp. 2), 1169–1170 (1985). The sap of this plant has been long used as a folk medicine for the treatment of skin cancer. Nowicky's thiophosphoric acid triaziridide derivative of an alkaloid from this plant, Ukrain, is water soluble and stable. Its structure is shown in FIG. 6.

The biological activities of Ukrain have been extensively studied. In 1984, Nowicky reported that over 100 cancer patients had been treated with this drug. Complete remission was experienced by some of the patients. Tumor regression was associated with an almost immediate, post-injection sensation at the site of the tumor, ranging from warmth to stabbing pain. Conversely, in patients not experiencing an immediate physical response, there was no observable antitumor response. It is hypothesized that in those patients whose tumors contained significant numbers of tumor-infiltrating lymphocytes and macrophages, the Ukrain stimulated the cells to release cytokines locally, causing the localized sensations and subsequent antitumor effects.

The antitumor effects of Ukrain were also observed in dogs with spontaneous tumors, Nowicky et al., "Biological activity of Ukrain in vitro and in vivo," Proceedings of the V Mediterranean Congress of Chemotherapy. Chemioterapia 6 (Supp. 2), 683–685 (1987). In these animals, the antitumor effects were also associated with observable physical manifestations, occurring immediately after intravenous administration of the drug. Spontaneous tumors in dogs have also been treated with the biomodulator pokeweed mitogen. Observations parallel those made by Nowicky et al. with Ukrain.

Preferred compounds include 3S,5R-colletruncoic acid and the compound obtained by switching the heptanoate chain of 3S,5R-colletruncoic acid with the adjacent methyl group on the ring.

Biomodulator Activities

Cellular functions can be broadly divisible into two general categories: proliferation (reproduction) and differentiation (specialization of function). According to present theory, the proliferative function is continuously present in the normal cell, and is dominated in the mature cell by the differentiative function, which thus acts as an integrative force to regulate both differentiative and proliferative functions in the mature cell. A failure in the biochemical mechanisms upon which the cell is dependent for control of cell differentiative and proliferative functions thus has important implications, as disruption of normal differentiative and proliferative controls may result in both abnormal cellular function and abnormal cellular growth regulation. Thus, improperly enhanced cellular proliferation, particularly when coupled to impaired cellular differentiation may be a basis for neoplasia. Similarly, the well-known phenomenon of cellular senescence couples a failure of proliferation of terminally differentiated cells after a defined number of cellular generations.

Without wishing to be bound by theory, biomodulators exert their effects at the most fundamental level by influencing cellular differentiation behavior, particularly abnormalities therein. They, for instance, can induce differentiation by modulating expression of the cellular differentiative phenotype; inter alia, the biomodulators induce expression of unexpressed genes to significantly diversify cellular function, or to significantly increase existing cellular function. The biomodulators are believed to induce proliferation in senescent cells by biomodulating expression of the cellular proliferative phenotype by similar mechanisms. Overall, the biomodulators counteract aberrant proliferative or differentiative cellular function by stimulating intracellular biochemical controls to normalize cellular behavior. It is this ability of biomodulators to normalize abnormal cellular function, both differentiative and proliferative (usually indirectly by normalizing aberrant differentiative activity underlying the aberrant proliferation, but also directly, e.g., in the case of senescent cells), across a wide spectrum of cell types, which primarily underlies their usefulness.

The biomodulators effect their results in very low concentrations and are generally characterized by a relatively low (less than 1,000 daltons) molecular weight, higher weights, however, also being involved in some cases. The compounds are non-toxic in the amounts employed in the methods of the present invention. It is theorized that these compounds simulate or involve mechanisms controlling cellular differentiative behavior and/or integration of cell proliferation and differentiation activity on a primitive level, thus accounting for their influence on a broad range biological effects.

As mentioned, one of the effects which biomodulators have been demonstrated to possess is their ability to normalize cellular function in cells which have become aberrant, e.g., tumor cells or senescent cells. In particular, from a mechanistic perspective, it has been shown that administration of biomodulators affects the conformational arrangements of simple cell-surface oligosaccharide structures in aberrant cells (Mann, P. L., et al., Mech. Ageing Devel., 44, 17–33 (1988). This has been shown, for example, by determination of binding-class affinities and capacities for specific lectin/oligosaccharide combinations, with and without biomodulator influence. Scatchard analysis and the calculation of Gibb's Free Energy (ΔG) were used for comparison purposes, as disclosed therein. The ΔG values obtained were found to be predictors of phenotypic changes and the efficacy of the biomodulators.

Characterization of the nature of these effects on the conformation of the cell-surface oligosaccharide displays was performed, inter alia, by NMR spectroscopy on cells in culture, both aberrant and normal. It was found that cells which are about to undergo senescence, and thus are failing in their proliferative function, showed a significant narrowing in proton linewidth measurements of cell surface water, which was correlated with a "down-regulation" of the ΔG value of the cell surface oligosaccharide display. Treatment of the cells with biomodulators prevented the "down-regulation" and NMR proton linewidth changes, as well as the subsequent development of the senescent phenotype. On the other hand, neoplastic cells have cell surface oligosaccharide displays which are "in-between" those of normal and senescent cells, both in terms of ΔG values and the proton linewidths. Treatment of these cells with biomodulators "up-regulates" the oligosaccharide conformations, increases linewidth values, increases the ability of these cells to be recognized by cytotoxic lymphocytes (the normal phenotype) and decreases their generation times in vitro.

Another primary characteristic of biomodulators (the other is the ability to alter cell surface oligosaccharide display as discussed above) is their immunostimulatory activity at the low doses discussed herein, e.g., as measured in assays discussed in application Ser. No. 07/694,321, measuring increased production of specific and non-specific antibodies from human peripheral blood leukocytes. Analogously, immunostimulatory effects of Ukrain have been noted in vitro, Nowicky, "Activation of Specific Lymphocyte and Leucocyte Clones with 'Ukrain'," Cancer Detection and Prevention 8, 549 (1985) and in vivo in cancer patients, Staniszeweski et al., "Immunological Profile in Patients with Small-Cell Lung Cancer (SCLC) Treated with Alkaloid Derivative from *Chelidonium Majus*" (Preprint), as well as in Austrian governmental filings in support of product registration. Ukrain has also been found to be somewhat cytotoxic to cancer cells, Boyd, National Cancer Institute Developmental Therapeutics Program in vitro screening data review checklist (Sep. 29, 1990), but its cytotoxicity is not sufficient to explain the observed anti-cancer response in humans and dogs. This is because its observed anti-cancer effects are assumed to be related to its function as a biomodulator as defined herein.

Typically, the biomodulators will selectively accumulate in areas of the body containing abnormal tissue. This occurs, it is theorized, because of the ability of biomodulators to normalize aberrantly differentiating cells. Thus, the biomodulators will concentrate in and around such cells on which they are active, whereby they will have effect on such environments and not others. In some cases, a biomodulator may concentrate in normal tissue. In such event, which particular tissue is the target of a particular biomodulator will be routinely determinable by preliminary experiments involving administration of the biomodulator followed by conventional body scans by an imaging modality sensitive to the presence of a biomodulator, e.g., MRI as discussed in related application 07/694,325.

The biomodulator approach to enhancing uptake of antibodies or conjugates thereof is based on the observation that certain biomodulators cause localized responses in tumors. Radiolabeled proteins administered or present during the response are expected to show altered tissue distribution, including enhanced uptake and more rapid blood clearance, with better tumor-to-non-tumor ratios of antibody uptake. As with all theories discussed herein, without wishing to be bound thereby, it is further theorized that the beneficial effects underlying this invention are attributable to the discussed reaction of the biomodulators with the oligosaccharide display on abnormal tissue infiltrating lymphocytes and/or macrophages and/or other cells, causing these cells to release cytokines locally within the tumor. Cytokines, in turn, can induce local changes that increase vascular permeability and extracellular fluid volumes, causing, e.g., rapid swelling, reddening and focal temperature increases. These responses appear similar to those observed with the prior art administration of interferon or IL2, except that the responses are more localized to the tumor or other abnormal tissue site.

Because of the ability of biomodulators to selectively concentrate in abnormal or other tissue, they can be used as "targeting molecules," by preconditioning such tissue in a fashion such that an agent (therapeutic or diagnostic) interacting with such tissue will do so in a way different from that with tissue not pretreated with a biomodulator.

Thus, where the tissue interaction of an active agent (diagnostic or therapeutic) is unsatisfactory or non-optimal, administration of the agent and a biomodulator per this invention will affect its performance, e.g., by enhancing uptake of the agent, e.g., by the above-discussed theorized mechanism of localized cell activation and concomitant intra-tumor vasodilation. This is a valuable effect since any increase in target-to-non-target ratios is significant in imaging or therapy, especially where the same is achieved without additional conjugation to an antibody using non-toxic materials (biomodulators). However, within the broadest scope of this invention, also included are situations wherein the biodistribution of the active agent in the target area is modified without necessarily involving increased uptake into the abnormal tissue, e.g., a tumor. In such cases, the resultant different distribution will provide valuable information since two "views" of the subject tissue will thereby be made available. Moreover, the biomodulators of this invention will also affect the retention/clearance rates of the agent, thereby providing variability in timing of, e.g., a sequence of images and in staging the state of the subject time.

Suitable antibodies for use in this invention are any which, when administered without a biomodulator, preferentially interact with particular tissue (target tissue) in an area vis-a-vis other tissue (non-target tissue) in the area. Such antibodies are conjugated with imaging-sensitive moieties which include many moieties of all modalities which enhance the contrast of an image thereof; therapeutic agents, e.g., drugs and radionuclides; etc. Particularly preferred antibodies for use in this invention are monoclonal antibodies, including, e.g., radiolabeled or antibody conjugates, e.g., antibodies bonded in any fashion to an imaging sensitive moiety, e.g., a metal or other chemical entity affecting an imaging modality; or to a chemical entity exerting a therapeutic effect, e.g., a radioactive metal or a drug, etc.

The term "antibody" as used herein includes antibodies, either poly- or monoclonal, fragments thereof, or an oligo- or polypeptide which is functionally equivalent to an epitopic antibody binding site and which is attached to a moiety, e.g., another protein or portion thereof or to a metal, which moiety is easily labeled by a group detectable by an imaging sensitive modality or which binding site is directly conjugated to a therapeutic agent. These agents can be constructed, e.g., according to conventional procedures, e.g., by fusion protein technology. Suitable preferred classes of agents are those produced by genetic engineering or chemical synthesis which have specific binding or targeting properties equivalent to those of antibodies, such as radiolabeled chemotactice peptides which localize at sites of infection. A. J. Fischman et al., J. Nucl. Med. 32, 483–491 (1991)

Suitable antibodies are any which are specific for local antigenic determinants present in the target tissue, including antibody fragments, e.g., F(ab')$_2$ or Fab fragments. The antibodies and antibody fragments can be obtained from conventional sources by conventional means, including by well known monoclonal antibody techniques and conventional recombinant DNA methods for producing particular proteins in high yields. Many examples of such immuno components are well known; e.g., antibodies and/or antibody fragments directed to the antigens of human chorionic gonadotropin (hCG), hCG $\alpha$-subunit, hCG $\beta$-subunit; other tumor-specific or tumor-associated molecules, including carcinoembryonic antigen (cEA), $\alpha$-fetoprotein (AFP), human melanoma-associated antigens, human sarcoma-associated antigens, etc. Similarly, examples of tumor-specific agents include monoclonal antibodies, antibody fragments, molecules which are a copy of an antibody binding site, or molecules which are a copy of an antibody binding site fused with or conjugated to a metal binding moiety or a drug moiety. K. F. Mitchell et al., "Hybridoma Antibodies Specific for Human Tumor Antigens," Monoclonal Hybridoma Antibodies: Techniques and Applications, J. G. R. Hurrell ed., CRC Press, Boca Raton, Fla., pp. 151–168 (1982). Additional examples of tumor-specific agents include proteins such as those described by Soria, Pharmacol. Res., 21, Supp. 2, 35–46 (1989) and Butt et al., J. Biol. Chem., 263, 16364–16371 (1988); and single polypeptide chain binding molecules, R. C. Ladner et al., U.S. Pat. No. 4,946,778, issued Aug. 7, 1990. See also J. G. McAfee, "Update on Radiopharmaceuticals for Medical Imaging," Radiology 171, 593–601 (1989).

Methods of binding such antibodies agents to imaging sensitive moieties or therapeutic agents are also very well known, both with cleavable and non-cleavable linkers. See, e.g., Alvarez et al., U.S. Pat. No. 4,741,900; EP-A-0 188 256, 0 289 187, 0 203 764; Sela et al. (U.S. Pat. Nos. 4,093,607 and 4,263,279); Schwartz (U.S. Pat. No. 4,647,671); Shen et al. (U.S. Pat. No. 4,631,190); Desphande et al., Intl. J. Red. Appl. Instrum. [B] (England) 16, 587–597 (1988); Quadri et al., J. Nuc. Med. 27, p. 959 (Absr. #337) (1986); Hoseman et al., J. Nuc. Med. 12, 455–460 (1986); and Meares et al., Intl. J. Cancer [Suppl.] U.S. 2, 99–102 (1988). A. R. Fritzberg et al., "Specific and Stable Labeling of Antibodies with Technetium-99m with a Diamide Dithiolate Chelating Agent," Proc. Natl. Acad. Sci. 85, 4025–4029 (1988); D. A. Scheinberg et al., "Tumor Imaging with Radioactive Metal Chelates Conjugated to Monoclonal Antibodies," Science 215, 1511–1513 (1982); A. R. Fritzberg, "Advances in $^{99m}$Tc-Labeling of Antibodies," Nucl. Med. 26, 7–12 (1987); D. J. Hnatowich et al., "DTPA-Coupled Proteins—Procedures and Precautions," Nucl. Med. Biol. 14, 563–568 (1987). Similarly well known are other imaging and therapeutic moieties to be attached to such antibodies from all fields of diagnostics and therapeutics.

Other methods of binding the active moiety to the antibody of course can also be used. Thus, radio-active iodine can be exchanged conventionally with non-radioactive iodine on the active agent. Other radio-active species, e.g., $^{99m}$Tc, etc., can be bonded, e.g., via conventional "tagging" procedures well known in the art, e.g., according to Rhodes, U.S. Pat. No. 4,305,922; Crockford et al., U.S. Pat. No. 4,424,200; Alvarez et al., U.S. Pat. No. 4,741,900; EP-A-0 188 256; EP-A-0 289 187; EP-A-0 203 764. For direct labeling of antibodies with $^{99m}$Tc: B. Rhodes, "Direct Labeling of Proteins with $^{99m}$Tc," Nucl. Med. Biol. (in press); $^{99m}$Tc generally: W. C. Eckelman et al., "Three Approaches to Radiolabeling Antibodies with $^{99m}$Tc," Nucl. Med. Biol. 16, 171–176 (1989); other radiolabels generally: D. J. Hnatowich, "Recent Developments in the Radiolabeling of Antibodies with Iodine, Indium, and Technetium," Semin. Nucl. Med 20 80–91 (1990); A. R. Fritzberg et al., "Approaches to Radiolabeling of Antibodies for Diagnosis and Therapy in Cancer," Pharm. Res. 5, 325–334 (1988).

For example, suitable agents active for various imaging modalities (for use in this invention when attached to antibodies or other targeting agents), include, for example, for MRI, paramagnetic substances, e.g., chelated metal ions, e.g., of atomic numbers 21–29, 42, 44 and 58–70, inter alia, particularly gadolinium, iron, manganese, dysprosium, etc.; for X-ray imaging, iodinated-benzene-based compounds, or heavy metals, e.g., of atomic numbers 21–29, 42, 44 and 57–83, inter alia; for radionuclide, e.g., gamma camera imaging (or radiotherapy, also), to radioactive ions, e.g., in chelated form or otherwise bound to an antibody, such as cobalt, technetium, strontium, copper, iodine, e.g., $^{123}$I or $^{131}$I, or Indium or gallium, etc.; for PET (positron emission tomograph), to positron emitting isotopes, such as $^{43}$Sc, $^{52}$Fe, $^{55}$Co, $^-$Cu etc. The chelating ligand can be EDTA, CDTA, DTPA, DOTA, TTHA, or any substituted derivative of the above. Using the biomodulators of this invention, there will be produced image enhancement by the corresponding modality, MRI, X-ray, radioimaging, PET imaging, etc. For MRI, the underlying physical phenomenon being measured can be any of the known parameters including $T_1$, $T_2$, proton density, chemical shift, etc.

Suitable therapeutic moieties, e.g., drugs or radioactive elements, are well known in the art. Suitable such drugs include antitumor agents such as Ara-C, Melphalan, Methotrexate, and other folate analogs, Daunomycin, Doxorubicin, Mitomycins, Bleomycins, Mitoxantrone, Dactinomycin, etc., as well as toxins such as ricin, abrin, diphtheria toxin, Pseudomonas exotoxin A, ribosomal inactivating proteins, mycotoxins, etc., but not limited thereto. Also applicable is a wide variety of other drug types, e.g., therapeutic agents in all of the major therapeutic areas including, but not limited to, anti-infectives, such as antibiotics and antiviral agents, analgesics and analgesic combinations, anthemidines, antiarthritics, antiasthmatic agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, beta-blockers, antiarrythmics, antihypertensives, diuretics, vasodilators including general, coronary, peripheral and cerebral, central nervous system stimulants, cough and cold preparations, decongestants, hormones, hypnotics, immunosuppressives, muscle relaxants, parasympatholytics, parasympathomimetics, psychostimulants, sedatives and tranquilizers.

The conjugation of the targeting to the imaging active moiety can be accomplished using any of the conventional techniques. Generally, where a metal is involved this can be accomplished by attaching the metal to a binding molecule, typically a chelating agent. The resultant chelate is bound to the targeting agent. The order of these binding reactions is not critical. For instance, a chelate structure can be bound to a targeting agent by means of a substituent on the non-critical ring portion or other non-critical portion of a targeting agent as described below. Typical substituents include OH, COOH, $NH_2$, $CONH_2$, and many others. Linking the targeting agent to the labeling agent, e.g., the chelating agent, or to the drug can be by means of any of a host of conventional linkers. For thorough descriptions of useful chelating agents, linking moieties, chemical methods for effecting the couplings, etc., see, e.g., U.S. Patent Nos. 4,352,751, 4,176,173, 4,310,507, 4,668,503, 4,986,979, 4,454,106; GB 2,109,407A; G. E. Krejarek et al., Bioch. Biophy. Res. Comm. 77, 581 (1977); Sela et al. (U.S. Pat. Nos. 4,093,607 and 4,263,279); Schwartz (U.S. Pat. No. 4,647,671); Shen et al. (U.S. Pat. No. 4,631,190); Desphande et al., Int. J. Rad. Appl. Instrum. [B] (England) 16, 587–597 (1988); Quadri et al., J. Nuc. Med. 27, p. 959 (Absr. #337) (1986); Hoseman et al., J. Nuc. Med. 12, 455–460 (1986); Meares et al., Intl. J. Cancer [Suppl.] U.S. 2, 99–102 (1988); D. J. Hnatowich et al., Science 220, 613 (1983); Manabe et al., Biochim. Biophys. Acta 883, 460 (1986).

Thus, the biomodulators can be administered in accordance with this invention for the enhanced visualization of any portion of the body in which a given biomodulator is determined to concentrate, especially those suspected of being in an aberrant state in view of the general capability of biomodulators to concentrate therein, e.g., especially for the visualization of tumors or for the enhanced treatment of such portions for the same reasons. Such abnormal tissue includes preferably cancerous and benign tumors such as soft tumors, such as leukemias and lymphomas, and solid tumors, such as melanomas, ovarian tumors, cervical tumors, breast tumors, lung tumors (small cell and non-small cell), colon and stomach tumors, hepatocellular tumors, pancreatic, midgut, bladder and prostate tumors, brain tumors, myelomas, and larynx tumors; but also senescent tissues and cells; injured tissue, especially containing endothelial cells for which biomodulators will enhance repair; defective immune cells; etc. Thus, this invention facilitates patient management by enabling the staging and evaluation of the extent of these aberrant states, such as metastasis of a tumor and treatment thereof. J. W. Nowicky et al., "Macroscopic UV-Marking through Affinity," J. Tumor Marker Oncology 3, 463–465 (1988) demonstrate the property of biomodulators to concentrate or target malignant tissue. PWM has also been shown to localize in areas of arthritis and in tissues affected in autoimmune disease (see related application Ser. No. 07/694,325).

By "abnormal tissue" herein is meant any tissue in a condition other than normal for a healthy host, e.g., mammals including humans, e.g., cancerous, diseased, injured, etc. Also included is senescent tissue whether due to the "normal" aging process or otherwise.

The imaging agents as described above can be administered in a manner fully analogous to conventional administration of imaging agents, e.g., as described in Enhanced Magnetic Resonance Imaging, V. M. Runge, ed., C. V. Mosby Co. (1989) for MRI, in EP 188,256; Kozak et al., TIBTEC October 1986, 262; Radiotracers for Medical Applications, CRC Press, Boca Raton, Fla., e.g., for radiodiagnostics and/or for radiotherapy, in Positron Emission Tomography of the Brain, Springer Verlag 1983, for PET, and in D. P. Swanson et al., "Pharmaceuticals in Medical Imaging," Macmillan Publishings Co., Inc., New York (1990); for X-ray, in each case for imaging of various tissues described above. For example, they are typically administered prior to the performance of the imaging procedure. It is even possible for the administration to be simultaneous with the imaging where desired, e.g., in pharmacokinetic studies. The optimum time periods required for preadministration of the biomodulator to achieve localization and/or preconditioning at the target site and resultant optimum image enhancement or modification will also vary with biomodulator and/or imaging agent and/or tissue and/or imaging modality and will also be routinely determinable. Of course, imaging will occur prior to significant clearance of the biomodulator from the site, which time period can also be routinely determined by those of skill in the art. Typically, biomodulators will be administered 15 minutes to 4 hours prior to administration of the imaging agent which will be administered in a normal time period prior to performing the imaging procedure, e.g., 15 minutes to 1 hour before. The short time periods for biomodulator preadministration are derived from the advantage that they are localized rapidly at their target sites and then cleared rapidly therefrom, as discussed further below. Longer or shorter time periods are also applicable, as long as the effect of the biomodulator on the target tissue is still active when the active agent becomes bioavailable to such tissue. The foregoing principles are fully analogously applicable to administration of a biomodulator with a tissue-specific therapeutic agent.

The agents of this invention may be administered alone, or more typically they may be administered in combination with one of the usual physiologically acceptable excipients, e.g., water, buffers, surfactants, etc., by the usual routes, e.g., enterally, parenterally, e.g., i.v., i.m., subcutaneously. The optimum amount of the biomodulator and the imaging agent may vary with the patient, the method of imaging or therapeutic treatment employed, the location to be imaged or treated, the timing of imaging or treatment, the active agent used, etc., and is routinely determinable by one of ordinary skill in the art. Typically, the amount of biomodulator dosed for all the uses discussed herein above and below will be in the same range of the amounts thereof effective for observance of the therapeutic and other physiological effects of the biomodulators per se, e.g., their effects of normalizing cellular differentiative abnormalities, e.g., typically, 100 ng/kg-100 µg/kg. The amounts of imaging agents will be essentially the same as those amounts usually employed with such agents or with analogous agents for the given imaging modality as conventionally performed, e.g., generally doses of 0.1 mmoles/kg or; generally doses as are well known and described, for example, in the reference material cited above. The amounts of therapeutic agent will be as in conventional treatment using the particular agent involved.

By the term "interact" herein is meant any chemical, physical or biological influence of one material on another, e.g., a bonding-type (weak or strong) relationship between two moieties, e.g., uptake of one moiety, e.g., an organ, by the other, e.g., tissue, or such as chemical attraction between a cellular oligosaccharide conformation (display) and an active agent in its vicinity. The biomodulator may be administered before, simultaneously with or after the administration of the tissue-specific, active agent, as long as the resultant tissue modification of this invention is in existence at some time during the contact thereof with the agent.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

Example 1

Effect of a Biomodulator on the Biodistribution of an Inactive Agent

Figure 2:
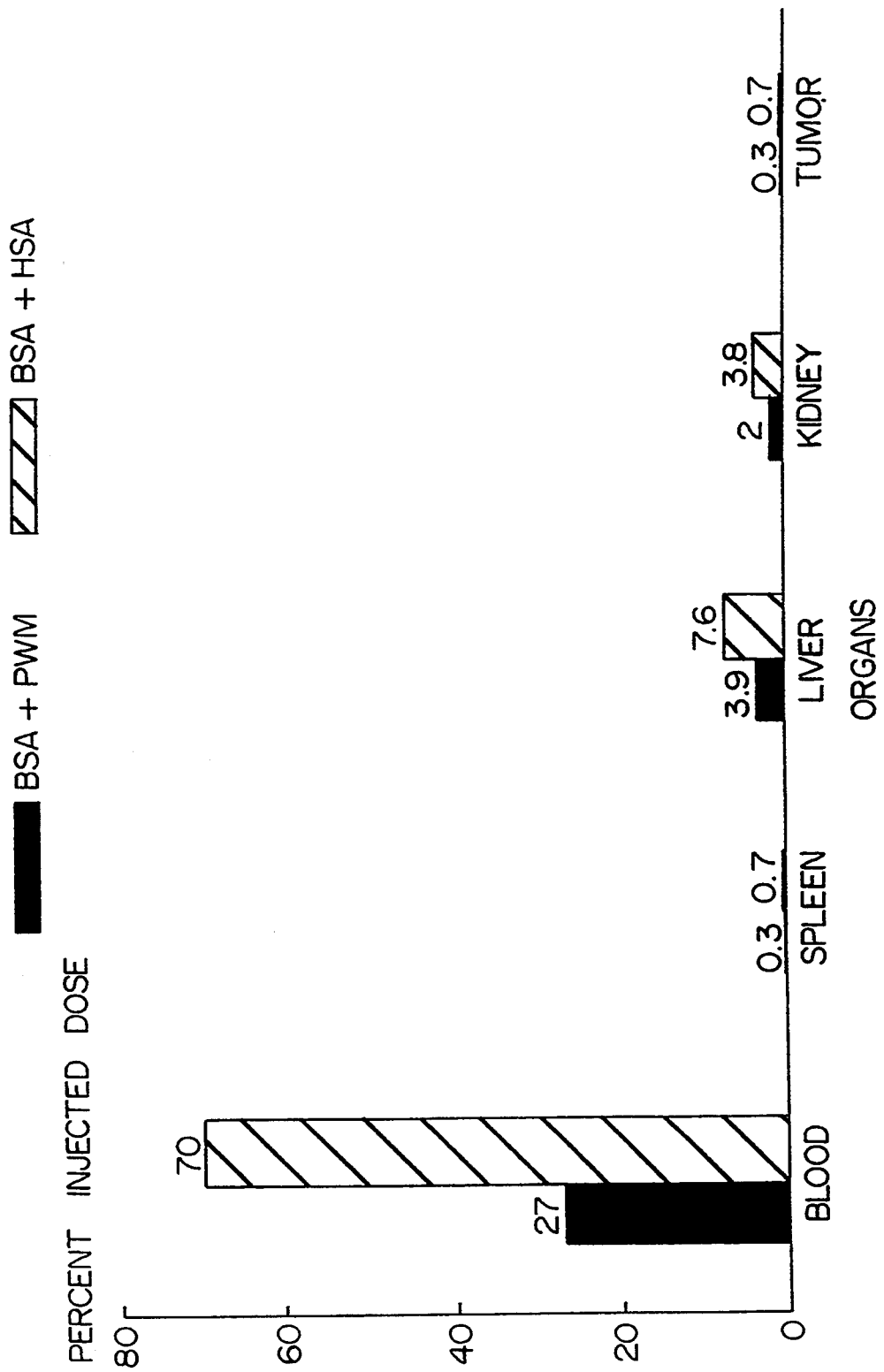

The results of biodistribution studies of mice injected with $6 \times 10^5$ B-16 melanoma cells 7 days prior to the injection of $^{99m}$Tc-labeled pokeweed ($^{99m}$Tc-PWM) and $^{125}$I-bovine serum albumin ($^{125}$I-BSA) or $^{99m}$Tc-labeled human serum albumin ($^{99m}$Tc-HSA) and $^{125}$I-bovine serum albumin ($^{125}$I-BSA). Biodistribution studies at 2 hours (FIG. 1) and at 4 hours (FIG. 2) show significant differences in the distribution of the $^{125}$I-BSA depending upon what it was co-injected with.

The pokeweed mitogen used in the tests of all examples herein was obtained by the method outlined in Waxdal, M. J., Biochem. 13, 3671 (1974).

Example 2

Figure 3:
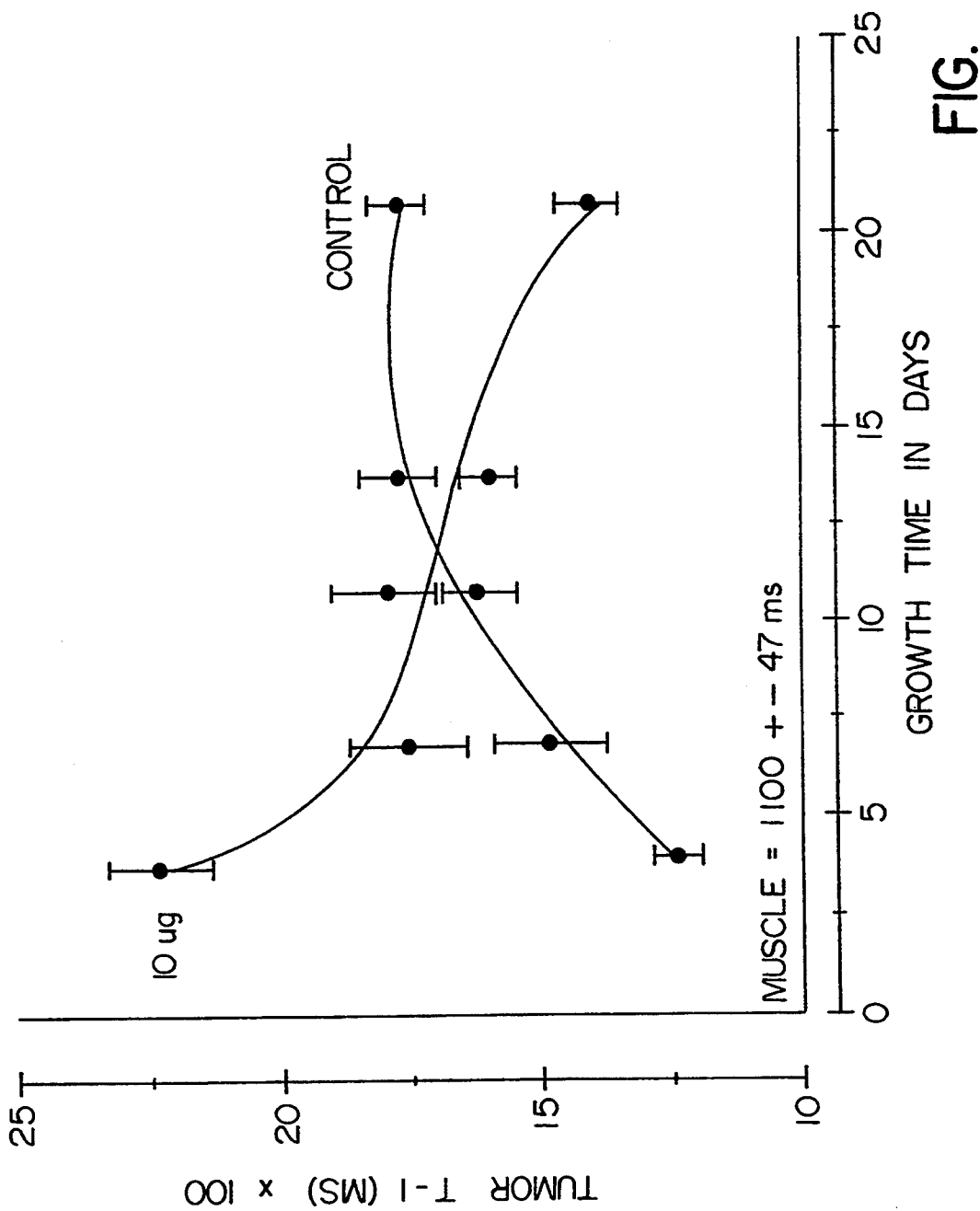
FIG. 3 shows the effect of injected PWM on tumor T-1.

Biodistribution Studies of Pokeweed Mitogen a. The effect on $T_1$ of unlabeled PWM An experiment was performed analogously to Example 1, but in nude rats with unlabeled PWM. FIG. 3 shows that the $T_1$ measured on the tumor was enhanced tenfold by treatment with PWM, while the $T_1$ of normal muscle tissue remained at baseline levels, demonstrating that PWM is specific to the tumor.

b. Tissue Distribution of $^{125}$I-labeled PWM

Ten different tissue samples bearing canine glioma cell tumors from rats which had been injected with $^{125}$I-PWM. Each corresponding set of samples were run through a set of two gels. One gel was stained in order to perform laser densitometry and the other was produced for autoradiography. After the tissue samples were run the distribution of radioactivity was assessed by precipitating all the protein with Trichloro Acetic Acid: Both the protein extract and supernatant were analyzed for percent radioactivity. After satisfactory results were obtained from the $^{125}$I count, the stained gels were put through the laser densitometer and the relative molecular weights of unknown proteins were then extrapolated from a graph of known molecular weight standards. The peaks from the densitometry were then counted and compared with each other to arrive at a relative percentage of total molecular weight.

Figure 4:
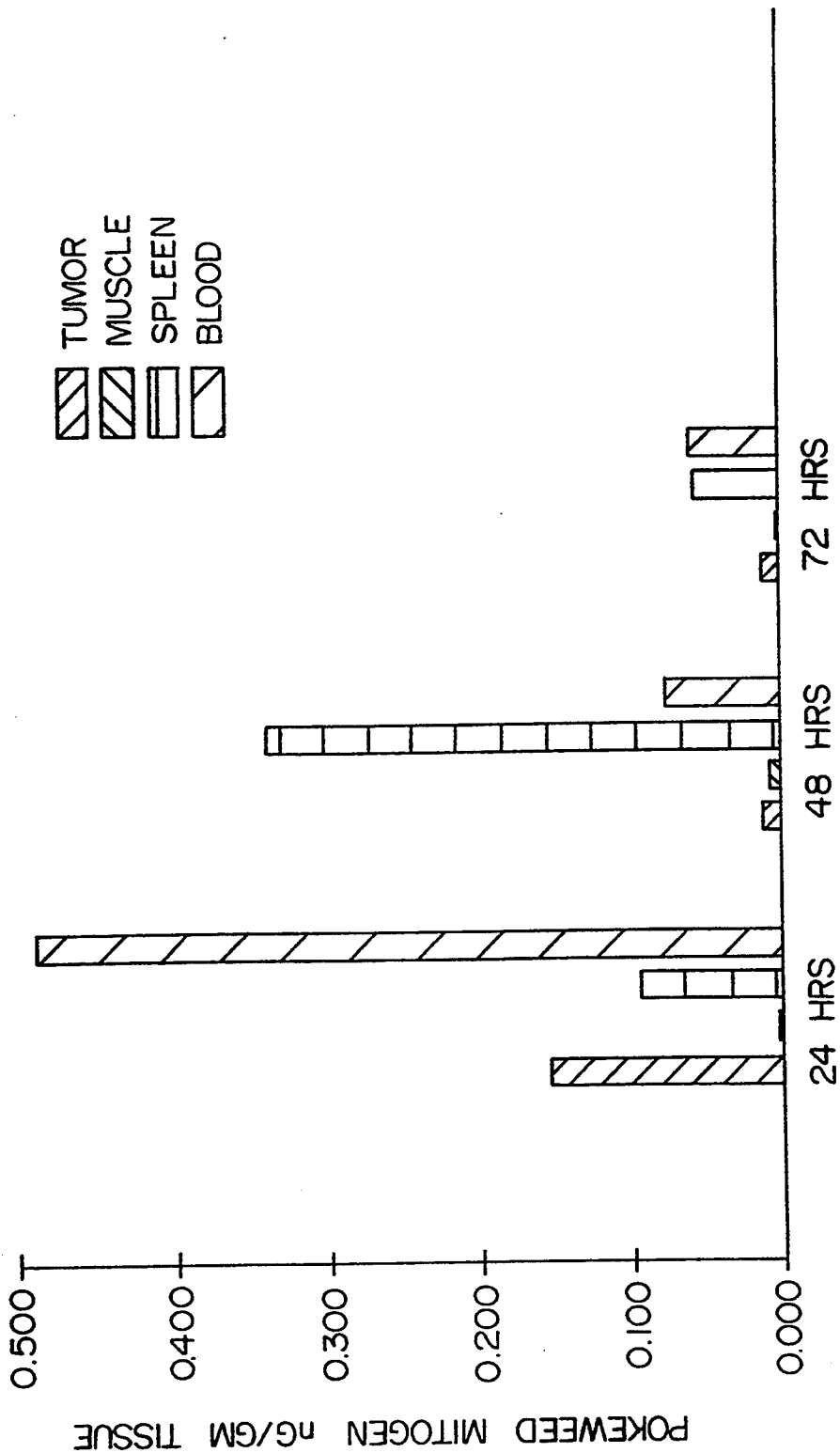
FIG. 4 is a plot of $^{125}$I PWM biodistribution at 24, 48 and 72 hours.

Thus, FIG. 4 shows that $^{125}$I-labeled PWM is taken up very specifically by the canine glioma tumor cells in the nude rat, and is also washed out very quickly by 48 to 72 hours.

c. Uptake of $^{99m}$Tc-PWM versus $^{99m}$Tc-HSA

Figure 5:
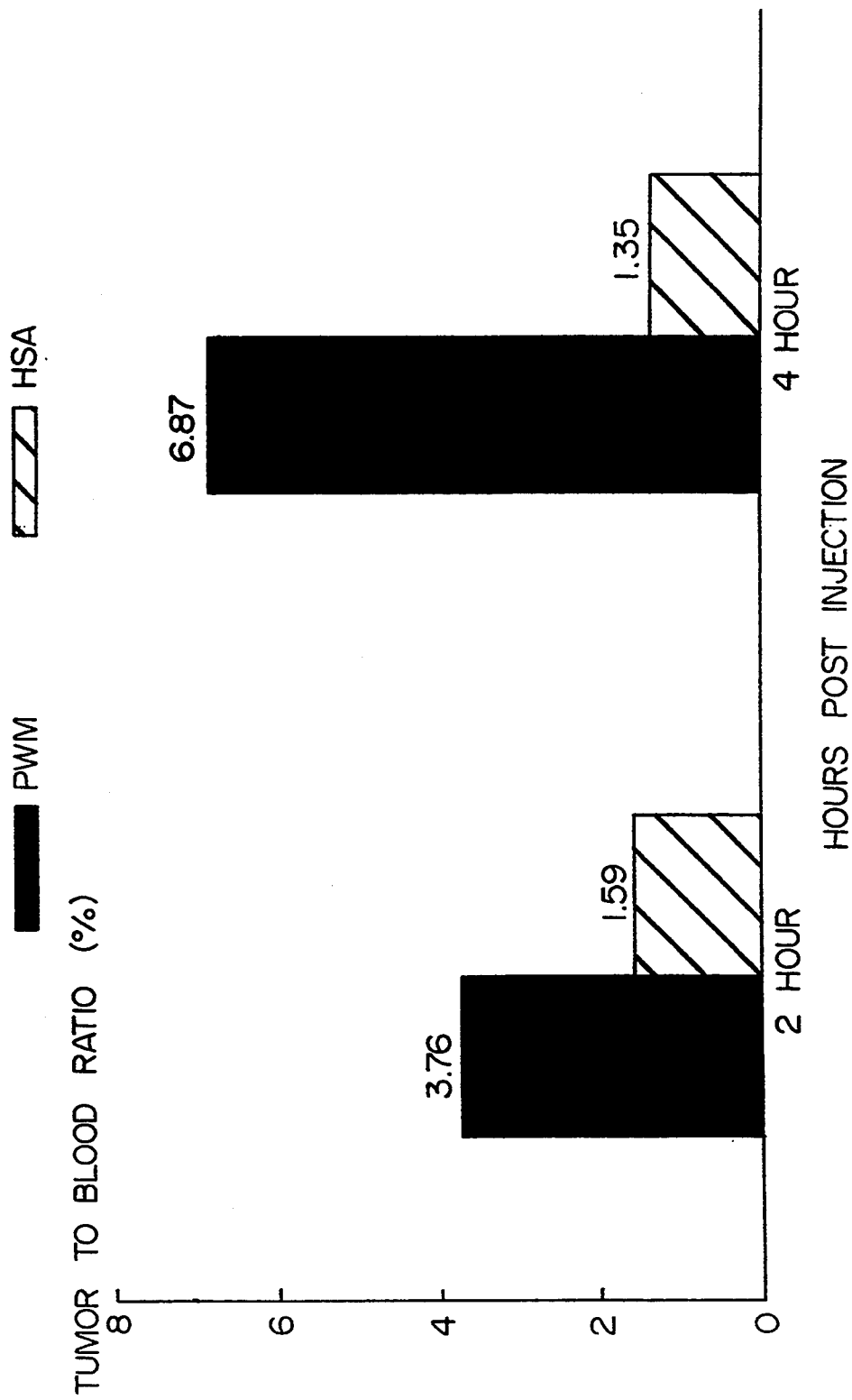
FIG. 5 is a plot of tumor-to-blood ratios of $^{99m}$Tc-PWM versus $^{99m}$Tc-HSA.

Mice were injected with B-16 melanoma cells 7 days prior to intravenous injection of $^{99m}$Tc-PWM or $^{99m}$TC-HSA (human serum albumin). Biodistribution studies were performed 2 and 4 hours later. At 2 hours post injection, the absolute percent uptake into the tumor was 0.41% for $^{99m}$Tc-PWM, and 0.35% for $^{99m}$Tc-HSA. At four hours post injection, the absolute uptake decreased to 0.25% of the injected dose for both agents. Visualization of the tumor, however, was not observed for the $^{99m}$Tc-HSA-labeled material, but was observed for the $^{99m}$Tc-PWM-labeled material. As can be seen from FIG. 5, the tumor-to-blood ratio for $^{99m}$Tc-PWM was significantly higher than the tumor-to-blood ratio for $^{99m}$Tc-HSA, providing a possible mechanism for the observed results.

Example 3

Imaging of Tumors with $^{99m}$Tc-Labeled Antibodies

In another preliminary study, two human tumor xenografts were implanted into contralateral hind legs of nude rats. One xenograft, LS-174T, expresses the colorectal antigens, CEA and TAG-72; the other xenograft, Canine glioma (CG), is negative for these antigens. Two groups of animals were studied. One group of rats received an I.P. injection of 10 µg of pokeweed mitogen 1 hour prior to the i.v. administration of 2 mCi (115 µg) of the monoclonal antibody, $^{99m}$Tc-chimeric B72.3. This antibody reacts with TAG-72 antigen on the LS-174T tumors. The animals were anesthetized, and the labeled antibody was administered through an isolated jugular vein. The animals were subsequently imaged at 0.5 hour intervals for 2 hours, to determine if early uptake could be enhanced. These animals were sacrificed at 2 hours post injection. The results of these early studies demonstrated a slight increase in antibody uptake by the LS-174T tumor. The number of observations and the differences were too small to be strictly statistically significant but the data are relevant for indicating the effect of the biomodulator.

Example 4

Optimization of Administration

A. Experimental Design and Methods

Biomodulators are prepared as described. In particular, the $^{99m}$Tc-labeled antibodies are prepared using either B72.3 (Schlom et al., Nucl. Med. Biol. 16, 137–142, (1989)) or anti-CEA, A5B7 (Blair et al., Brit. J.

Cancer 61, 891–894 (1990) and fragments of these antibodies. The radiolabeled products that are injected into mice are fully characterized with respect to yields of strongly bonded $^{99m}$Tc, total protein-bound $^{99m}$Tc, colloidal $^{99m}$Tc, free pertechnetate, and other $^{99m}$Tc species, if present (Rhodes, B. A., Nucl. Med. Biol. (in press)). Preparations with less than 90% of the $^{99m}$Tc strongly bonded to antibody protein are injected. The immunoreactive fractions of all preparations are also determined (Rhodes et al., BioTechniques 8, 70–74 (1990)).

B. Animal Model

The animal model is nude rats with implanted xenografts, LS-174T (expresses antigens recognized by antibodies B72.3 and A5B7) and CG (Canine glioma, negative for antigens recognized by antibodies B72.3 and A5B7). The two cell lines, CG and LS-174T, are seed-lotted, frozen, and are maintained in liquid nitrogen. The canine glioma (CG) is at passage 32. When needed cells are grown up in RPMI 1640 medium supplemented with 10% FCS (Flow Labs) and pen/strep (100 U/100 μg/ml), with subcultivation every 2–3 days. The growth is assessed by determining the generation time of the cells, which is the number of hours required for population doubling. This is calculated by dividing the log of the final cell count, minus the initial count, by the log of 2. The total culture time, in hours, divided by this value provides the generation time. This value is a measure of the stability of the culture. The cells are always used during log phase growth.

To passage each culture, cells are rinsed with Ca/Mg free phosphate buffered saline (PBS, pH 7.0), followed by a 2–5 minute exposure to 5 ml of 0.25M trypsin at 37° C. After all cells have detached, 5 ml of complete medium is added to the flask. Cells are centrifuged at approximately 200× g for 5 minutes, washed 1–3 times with medium, and counted on a hemocytometer. Staining aliquots with Trypan Blue provide an assessment of viability. Cell stock are assayed for Mycoplasma using the fluorometric technique regularly during the experiments, and later by the Mycotrim-TC assay system of Hana Biologics (Dupont, Inc.).

Nude rats weighing 150–200 grams are purchased from Harlan Sprague-Dawley (Indianapolis, Ind.) and maintained in a sterile environment. 0.6–0.8×10$^6$ cells are injected i.m. into the flank. The LS-174T cells are injected first because of their slower growth. After 1–2 weeks, when the tumor is palpable, the same number of CG cells are injected i.m. into the contralateral flank. About 10 days later both tumors are proper size for use in biodistribution studies.

Similarly, the tumor-bearing nude rats, into which fresh, sterile, human leukocytes are administered 24 hours prior to the biodistribution studies can be used to show the interaction with human leukocytes.

C. Biodistribution Studies

Two or three replicate (three animals) data points are used for each study. The optimum dose of Pokeweed mitogen has been established as 10 μg per animal. For Ukrain, the same 10 μg dose is used, and compared with 1 and 100 μg doses. Three administration sequences are tested: giving the biomodulator simultaneously with, 30 minutes prior to, and 30 minutes prior to the radiolabeled antibody. ANimals are sacrificed 24 hours post injection of the radiolabeled antibody. One group receives the biomodulator and there is a control group that receives antibody, but no biomod.

The animals are sacrificed by exsanguination while anesthetized, and tissue samples are then collected and weighed. The radioactivity of each tissue is determined by gamma ray scintigraphy. The percent injected dose per organ and per gram is calculated. A computer program for making these calculations is in routine use, and the use of appropriate controls and standards assures accurate biodistribution data. Also, tumor-to-non-tumor ratios are calculated for each of the tissues.

Mean and standard deviations are determined for each data point, and the Student's t statistic are used to test the hypothesis that pairs of data points are the same.

Using these techniques the following is determined:
1. The optimum time for injecting Pokeweed mitogen relative to the injection of the $^{99m}$Tc-labeled antibody;
2. The optimum time for injecting the thiophosphoric acid triaziridide derivative of *Cheldonium majus L.* alkaloid (Ukrain) relative to the injection of the $^{99m}$Tc-labeled antibody;
3. The dose response curves for Pokeweed mitogen and Ukrain in terms of absolute uptake of $^{99m}$Tc in both antigen-positive and antigen-negative tumors, and in terms of the target-to-non-target ratios; and
4. For the best biomodulator at the optimum dose and injection time, the biodistribution of the $^{99m}$Tc-antibody administered either as F(àb$^-$')$_2$ or as Fab' fragments.

Example 5

Pretreatment with Biomodulators Enhances Specificity of Labeled Antibody Binding to Tumor Tissue Mice are injected with CG tumor cells and tumors established as described in related application Ser. No. 07/694,321 CG-tumor-specific antibodies, produced according to standard methods, are labeled with $^{99m}$Tc as described herein, and injected into the mice, four hours after injection of 10 μg PWM. Control animals do not receive injection of PWM. Gamma camera images are obtained as described above. The PWM-treated animals show a higher specificity of labeling of the tumor tissue than the control.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of enhancing the delivery to abnormal tissue of an antibody-active agent which preferentially interacts with said abnormal tissue in comparison to neighboring normal tissue, comprising administering to a host a biomodulator and said active agent, the relative timing of the administration of each of the biomodulator and the active agent and their amounts being effective to enhance the preferential interaction of said active agent over neighboring normal tissue, wherein said biomodulator is a compound selected from CAD; swainsonine or an indolizidine alkaloid having an electronically similar 1,3-diol structure;

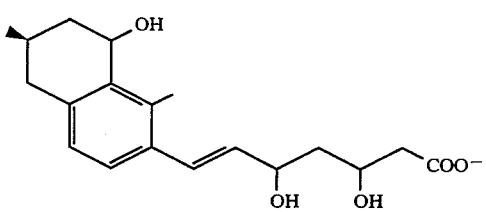

or

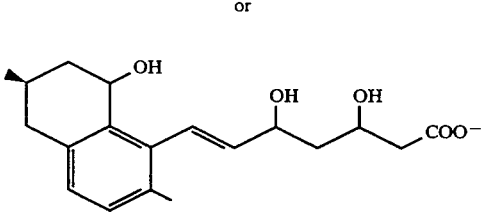

having a 3S,5R; 3R,5R; or 3S,5S stereoconfiguration; pokeweed mitogen; Ukraine; or a compound of formula (I)

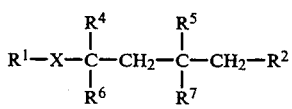

wherein

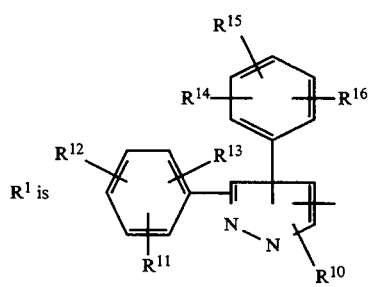

wherein $R^{10}$ is $C_{1-6}$-alkyl not containing an asymmetric carbon atom;

each of $R^{11}$ and $R^{14}$ is, independently, H, $C_{1-3}$-alkyl, n-butyl, i-butyl, t-butyl, $C_{1-3}$-alkoxy, n-butoxy, i-butoxy, trifluoromethyl, fluoro, chloro, chloro, phenyl, phenoxy or benzyloxy;

each of $R^{12}$ and $R^{15}$ is, independently, H, $C_{1-3}$-alkyl, $C_{1-3}$-alkoxy, trifluoromethyl, fluoro, chloro, chloro, phenyl, phenoxy or benzyloxy;

each of $R^{13}$ and $R^{16}$ is, independently, H, $C_{1-2}$-alkyl, $C_{1-2}$-alkoxy, fluoro or chloro;

with the provisos that not more than one of $R^{11}$ and $R^{12}$ is trifluoromethyl; not more than one of $R^{11}$ and $R^{12}$ is phenoxy; not more than one of $R^{11}$ and $R^{12}$ is benzyloxy; not more than one of $R^{14}$ and $R^{15}$ is trifluoromethyl; not more than one of $R^{14}$ and $R^{15}$ is phenoxy; not more than one of $R^{14}$ and $R^{15}$ is benzyloxy;

$R^2$ is —$CH_2OH$, —CHO, —$COOR^3$, —$COSR^3$, —$CONR^8R^9$ or the corresponding lactone

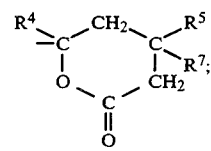

wherein $R^3$ is H or $C_{1-10}$-alkyl, $R^4$ and $R^5$ are each independently H or $C_{1-6}$-alkyl, $R^6$ and $R^7$ are each independently OR, NHR or SR wherein R is H or $C_{1-4}$-alkanoyl, $R^8$ and $R^9$ are each independently H or $C_{1-10}$-alkyl, and X is $C_{2-3}$-alkylene, $C_{2-3}$-alkenylene, $C_{2-3}$-alkynylene, a cyclopropylene group, —$OCH_2$— or —$SCH_2$—, wherein said compound is effective as a biomodulator.

2. A method of claim 1, wherein said active agent is a monoclonal antibody or a monoclonal antibody conjugated to an imaging or therapeutic agent.

3. A method of claim 2, wherein said antibody agent is conjugated and comprises a radiolabel.

4. A method of claim 2, wherein said abnormal tissue is a tumor.

5. A method of claim 3, wherein said abnormal tissue is a tumor.

6. A method of claim 5, wherein said method further comprises radioimaging said tumor.

7. A method of claim 4, wherein said agent is an antibody conjugated to a drug.

8. A method of claim 4, wherein said agent is an antibody conjugated to a moiety enhancing the contrast of an NMR, X-ray or PET image.

9. A method of claim 4, wherein the amount of said biomodulator is 100 ng/kg-100 µg/kg.

10. A method of claim 5, wherein the amount of said biomodulator is 100 ng/kg-100 µg/kg.

11. A method of claim 1, wherein the biomodulaton is pokeweed mitogen or Ukrain.

12. A method of claim 5, wherein the biomodulator is pokeweed mitogen or Ukrain.

13. A method of claim 1, wherein the biomodulator is administered 15 minutes to 4 hours prior to administration of said agent.

14. A method of claim 1, wherein the biomodulator is

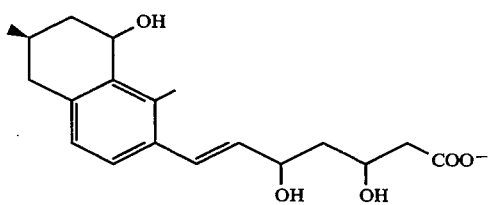

or

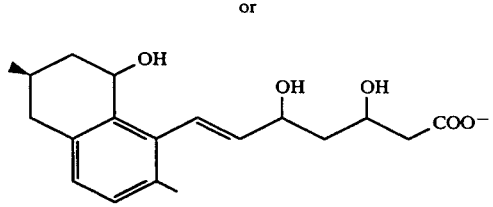

having a 3S,5R; 3R,5R; or 3S,5S stereoconfiguration.

15. A pharmaceutical kit comprising a container comprising a biomodulator and a separate container comprising an antibody or an antibody conjugated to an imaging or therapeutic agent, wherein said biomodulator is a compound selected from CAD; swainsonine or an indolizidine alkaloid having an electronically similar 1,3-diol structure;

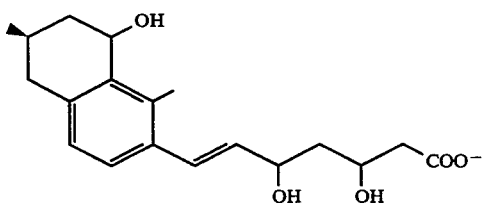

or

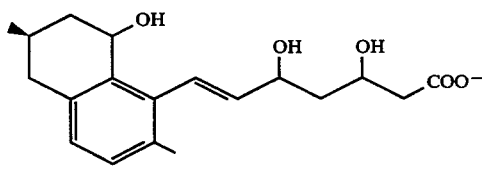

having a 3S,5R; 3R,5R; or 3S,5S stereoconfiguration; pokeweed mitogen; Ukraine; or a compound of formula (I)

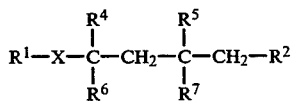

wherein $R^1$ is

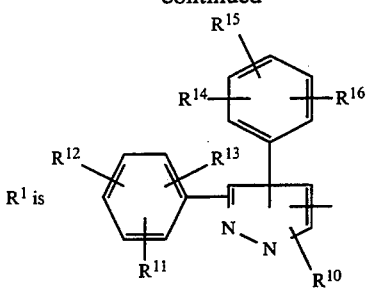

wherein $R^{10}$ is $C_{1-6}$alkyl not containing an asymmetric carbon atom;

each of $R^{11}$ and $R^{14}$ is, independently, H, $C_{1-3}$-alkyl, n-butyl, i-butyl, t-butyl, $C_{1-3}$-alkoxy, n-butoxy, i-butoxy, trifluormethyl, fluoro, chloro, chloro, phenyl, phenoxy or benzyloxy;

each of $R^{12}$ and $R^{15}$ is, independently, H, $C_{1-3}$-alkyl, $C_{1-3}$alkoxy, trifluoromethyl, fluoro, chloro, chloro, phenyl, phenoxy or benzyloxy;

each of $R^{13}$ and $R^{16}$ is, independently, H, $C_{1-2}$-alkyl, $C_{1-2}$-alkoxy, fluoro or chloro;

with the provisos that not more than one of $R^{11}$ and $R^{12}$ is trifluoromethyl; not more than one of $R^{11}$ and $R^{12}$ is phenoxy; not more than one of $R^{11}$ and $R^{12}$ is benzyloxy; not more than one of $R^{14}$ and $R^{15}$ is trifluoromethyl; not more than one of $R^{14}$ and $R^{15}$ is phenoxy; not more than one of $R^{14}$ and $R^{15}$ is benzyloxy;

$R^2$ is —$CH_2OH$, —CHO, —$COOR^3$, —$COSR^3$, —$CONR^8R^9$ or the corresponding lactone

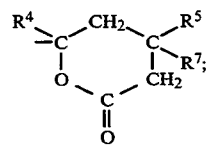

wherein $R^3$ H or $C_{1-10}$-alkyl, $R^4$ and $R^5$ are each independently H or $C_{1-6}$-alkyl, $R^6$ and $R^7$ are each independently OR, NHR or SR wherein R is H or $C_{1-4}$-alkanoyl, $R^8$ and $R^9$ are each independently H or $C_{1-10}$-alkyl, and X is $C_{2-3}$-alkylene, $C_{2-3}$-alkenylene, $C_{2-3}$-alkynylene, a cyclopropylene group, —$OCH_2$— or —$SCH_2$—, wherein said compound is effective as a biomodulator.

* * * * *